United States Patent [19]

Deckner et al.

[11] Patent Number: 4,813,962

[45] Date of Patent: Mar. 21, 1989

[54] HIP JOINT PROSTHESIS

[76] Inventors: Andre G. Deckner, 5, Rue de l'Harmonie F-75015, Paris, France; Martin Imhof, CH6343 Rotkreuz, Switzerland; Karl Zweymuller, Klinik, Garnisongasse 13, A-1090 Wien, Austria

[21] Appl. No.: 32,333

[22] Filed: Mar. 30, 1987

[30] Foreign Application Priority Data

Apr. 3, 1986 [CH] Switzerland ............... 1303/86

[51] Int. Cl.⁴ ............................................. A61F 2/32
[52] U.S. Cl. ................................................ 623/23
[58] Field of Search ............... 623/22, 23; 128/92 V, 128/92 VV

[56] References Cited

U.S. PATENT DOCUMENTS 3,801,989  4/1974  McKee .................... 129/92 V
3,973,278  8/1976  Shersher ..................... 623/22

FOREIGN PATENT DOCUMENTS 2475891  8/1981  France ......................... 623/22

Primary Examiner—Vincent Millin
Assistant Examiner—J. Welsh
Attorney, Agent, or Firm—Kenyon & Kenyon

[57] ABSTRACT

The prosthesis has a blade with a roof-ridge shaped shoulder at the proximal end adjacent to the neck. In addition, a bore is disposed in the shoulder on a medial plane so that a hook-shaped instrument can be inserted in to the bore from a direction of the neck. Movement and alignment of the blade via the insertion instrument is performed in the direction of the longitudinal axis of the blade.

9 Claims, 1 Drawing Sheet

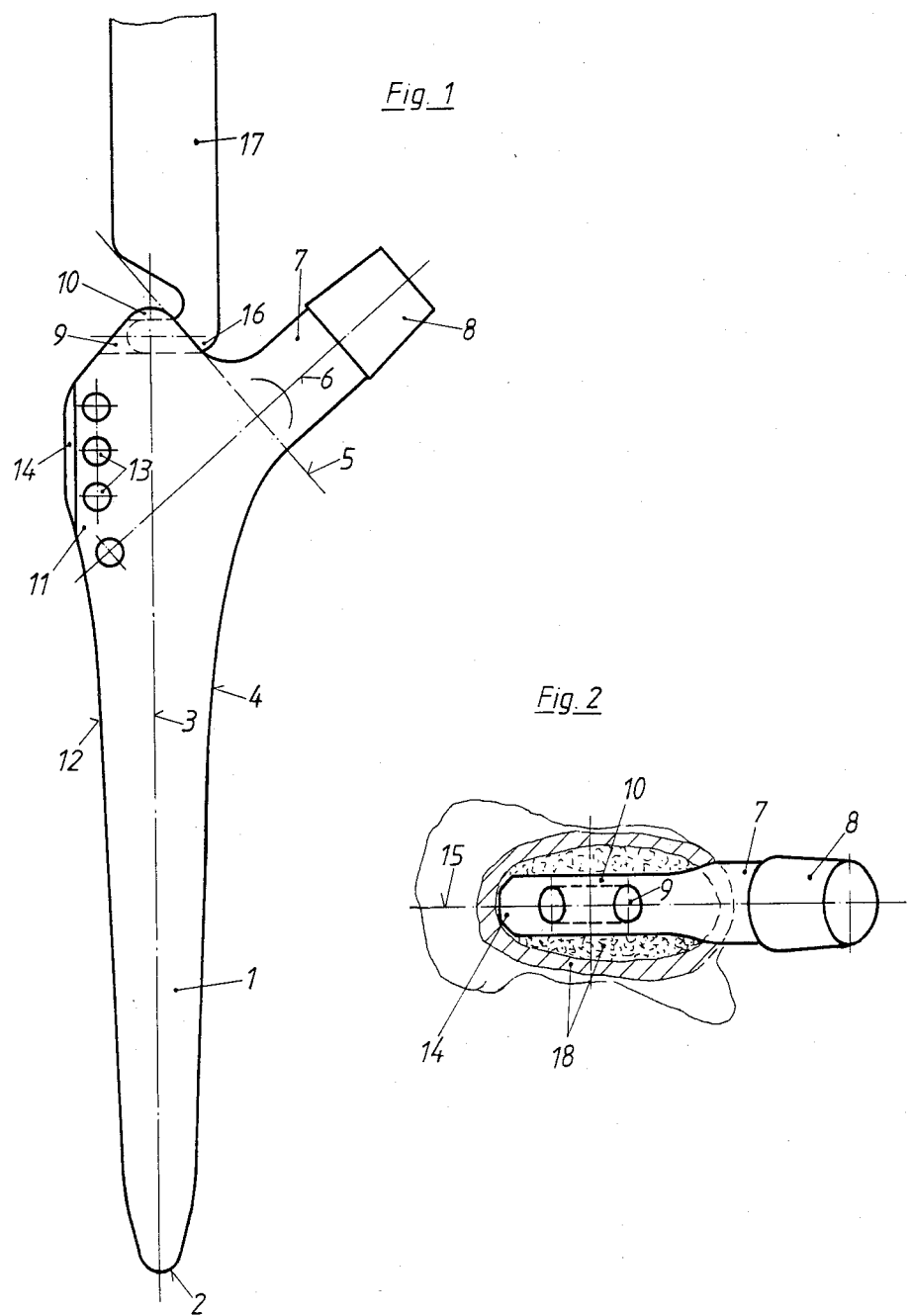

HIP JOINT PROSTHESIS

This invention relates to a hip joint prosthesis. More particularly, this invention relates to a hip joint prosthesis for anchoring in a femur.

Heretofore, various constructions have been used for anchoring a hip joint prosthesis in a femur. For example, as described in U.S. Pat. Nos. 4,404,993 and 4,422,187, prostheses have been known to have a blade-like shaft for anchoring in a femur in which a medial narrow side of the shaft terminates in a continuous curve at a prosthesis neck and which has a roof-ridge shaped proximal end. Generally, this type of prosthesis is used where a joint head prosthesis is to be anchored in a femur in a cement-free manner. Usually, fixation consists in jamming and wedging the shaft into the cortex of a surgically prepared femur. This jamming takes place primarily in the area of the diaphysis, that is, in the distal part of the shaft and requires that the surgical hollowed space and the shaft form and size be carefully matched and adjusted relative to each other. In some cases, it may also be necessary to remove and re-insert the shaft several times during a surgical procedure. For this reason, the shafts have been provided with a bore in the roof-ridge shaped proximal end which is perpendicular to the sides of the blade so as to permit the use of a hook-shaped instrument for pulling or driving out the shaft from the femur.

Generally, it is desirable to retain as much bone substance as possible when preparing a femur for the implantation of a joint head prosthesis. This is especially true in the area of the trochanter. However, because of the attachment of muscles and ligaments, difficulties may arise in the placement of a removal hook. This is because a hook may not be able to be "inserted" into the bore of a customary shaft without additional bone loss in the region of the trochanter.

Accordingly, it is an object of the invention to provide a prosthesis with a blade which permits insertion of a removal instrument in a trochanter area without difficulty and without additional bone loss.

It is another object of the invention to reduce the amount of bone loss in a femur for the implantation of a joint head prosthesis.

Briefly, the invention provides a prosthesis for a hip joint which is comprised of a neck and a blade which extends along a longitudinal axis and which is connected to the neck along a boundary plane disposed in angular relation to the longitudinal axis. In addition, the blade has a pair of opposite wide sides, a medial narrow side extending from the neck on a continuous curve, a lateral narrow side and a roof-ridge shaped shoulder between the lateral narrow side and the neck. In accordance with the invention, a bore extends in the shoulder on a median plane parallel to the wide sides of the blade.

The bore may be disposed perpendicular to the longitudinal axis of the shank and the longitudinal axis of the shank may be disposed on a straight line.

Further, the blade may have a distal section of conical shape which extends symmetrically along the longitudinal axis as well as a trochanter wing which extends between the shoulder and the lateral narrow side.

The neck may also be disposed on an axis perpendicular to the boundary plane.

With the positioning of the bore on the median plane, parallel to the wide sides of the blade, a removal instrument can be readily inserted into the blade from the direction of prosthesis neck without need to spread a bone resection to a greater extent than necessary for blade insertion.

The prosthesis construction offers the same advantages for repeat operations of previously implanted blades as well as for adjustment during a surgical procedure.

These and other objects and advantages of the invention will become more apparent from the following detailed description taken in conjunction with the accompany drawings wherein:

FIG. 1 schematically illustrates an anterior/posterior view of a prosthesis constructed in accordance with the invention; and FIG. 2 illustrates a view from above of the prosthesis of FIG. 1 after implantation in a femur.

Referring to FIG. 1, the prosthesis includes a blade 1 which extends from a distal end 2 along a longitudinal axis 3 which is disposed on a straight line. The blade 1 is connected to a neck 7 along a boundary plane 5 which is disposed in angular relation to the longitudinal axis 3 as well as in perpendicular relation to the axis 6 of the neck 7.

Referring to FIGS. 1 and 2, the blade 1 has a pair of opposite wide sides, a medial narrow side 4 which extends from the neck 7 on a continuous curve and a lateral narrow side 12 which extends on a conical taper from the distal end 2 to a trochanter wing 11. The wing 11, in turn, extends into a roof-ridge shaped shoulder 10 at the proximal end of the blade 1. As shown, the shoulder 10 is disposed symmetrically of the longitudinal axis 3.

The prosthesis is also provided with a peg 8 on the neck 7 for receiving a spherical joint head (not shown) as is known.

Referring to FIGS. 1 and 2, the shoulder 10 projects from between the lateral side 12 and the neck 7 and is provided with a bore 9 which extends on a median plane 15 (see FIG. 2) parallel to the wide sides of the blade 1 and through the shoulder 10. In the illustrated embodiment, the bore 9 intersects and extends perpendicular to the longitudinal axis 3; however, the bore 9 may also be placed obliquely to the longitudinal axis 3 so as to increase from the medial to the lateral.

As indicated in FIG. 1, the bore 9 is sized so as to receive a hook 16 of a removal instrument 17 (shown schemmatically) This hook instrument 17 may serve simultaneously for guiding and aligning the blade 1 while fitting the blade into a surgical opening. The angle of the hook 16 relative to the axis of the instrument 17 may, of course, be adjusted to the angle of the bore 9 relative to the longitudinal axis 3.

The trochanter wing 11 may also be provided with perforations or bores 13 which are disposed for identifying the prosthesis and/or for radiographic observations of the bone structure. The outer end of the trochanter wing 11 may also have a tapered area 14.

During a surgical procedure, the hook 16 of the instrument 17 can be readily inserted into the bore 9 without hinderance from the direction of the prosthesis neck 7 and without additional removal of bone substance 18 as indicated in FIG. 2. Further, should the prosthesis require removal, removal takes place in the direction of the longitudinal axis 3. For a straight blade, removal is perpendicularly upwards, as viewed; for a curved blade, removal is in accordance with the curvature of the longitudinal axis.

The invention thus provides a prosthesis with a bore which is particularly located so as to reduce the need for removing excess bone in order to position a removal instrument therein.

Further, the invention provides a prosthesis wherein a removal instrument can be readily inserted into a shoulder from the direction of the neck of the prosthesis.

What is claimed is:

1. a prosthesis for a hip joint comprising
   a neck; and
   a blade extending along a longitudinal axis and connected to said neck along a boundary plane disposed in angular relation to said longitudinal axis, said blade having a pair of opposite wide sides, a medial narrow side extending from said neck on a continuous curve, a lateral narrow side, a roof-ridge shaped shoulder between said lateral narrow side and said neck and a bore extending through said shoulder from lateral to medial on a median plane parallel to said wide sides for reception of a hook of a removal instrument from opposite sides in the direction of said neck.

2. A prosthesis as set forth in claim 1 wherein said blade has a distal section of conical shape extending symmetrically along said longitudinal axis.

3. A prosthesis as set forth in claim 1 wherein said bore is perpendicular to said longitudinal axis.

4. A prosthesis as set forth in claim 1 wherein said longitudinal axis is disposed on a straight line.

5. A prosthesis as set forth in claim 1 wherein said blade further includes a trochanter wing between said shoulder and said lateral narrow side.

6. A prosthesis as set forth in claim 1 wherein said neck is disposed on an axis perpendicular to said boundary plane.

7. A prosthesis as set forth in claim 1 wherein said shoulder is disposed symmetrically of said longitudinal axis and said bore is disposed perpendicularly on said axis.

8. A prosthesis as set forth in claim 1 wherein said bore intersects said longitudinal axis.

9. A prosthesis for a hip joint comprising
   a neck; and
   a blade extending along a longitudinal axis and connected to said neck along a boundary plane disposed in angular relation to said longitudinal axis, said blade having a pair of opposite wide sides, a narrow medial side, a narrow lateral side, a roof-ridge shaped shoulder at a proximal end of said blade projecting from between said lateral side and said neck on said axis and a bore extending through said shoulder from lateral to medial for reception of a removal instrument in the direction of said neck and from opposite sides of said bore.

* * * * *